(12) United States Patent
Planas et al.

(10) Patent No.: US 9,987,411 B2
(45) Date of Patent: Jun. 5, 2018

(54) METHODS AND SYSTEMS FOR PRIMING A BIOLOGICAL FLUID PROCESSING CIRCUIT

(71) Applicant: Fenwal, Inc., Lake Zurich, IL (US)

(72) Inventors: Samantha M. Planas, Wauconda, IL (US); Amit J. Patel, Algonquin, IL (US); Melissa A. Thill, Kenosha, WI (US); Christopher Wegener, Libertyville, IL (US); Elizabeth Asma, Durham, NC (US)

(73) Assignee: FENWAL, INC., Lake Zurich, IL (US)

( * ) Notice: Subject to any disclaimer, the term of this patent is extended or adjusted under 35 U.S.C. 154(b) by 198 days.

(21) Appl. No.: 14/577,283

(22) Filed: Dec. 19, 2014

(65) Prior Publication Data
US 2016/0177263 A1    Jun. 23, 2016

(51) Int. Cl.
*A61M 37/00* (2006.01)
*A61M 1/36* (2006.01)
*A61M 1/30* (2006.01)
A61M 1/02 (2006.01)
A61M 1/26 (2006.01)

(52) U.S. Cl.
CPC .......... *A61M 1/3644* (2014.02); *A61M 1/303* (2014.02); *A61M 1/3643* (2013.01); *A61M 1/0209* (2013.01); *A61M 1/265* (2014.02)

(58) Field of Classification Search
CPC .... A61M 1/34; A61M 1/3643; A61M 1/3644; A61M 1/303; A61M 1/0209
See application file for complete search history.

(56) References Cited

U.S. PATENT DOCUMENTS

| | | | |
|---|---|---|---|
| 5,178,603 A | * | 1/1993 | Prince ..................... A61M 1/30 604/6.01 |
| 5,591,344 A | | 1/1997 | Kenley et al. |
| 5,643,794 A | | 7/1997 | Liu et al. |
| 5,762,805 A | | 6/1998 | Truitt et al. |
| 5,776,345 A | | 7/1998 | Truitt et al. |
| 5,910,252 A | * | 6/1999 | Truitt ...................... A61M 1/16 210/103 |
| 5,951,870 A | | 9/1999 | Utterberg |
| 6,300,054 B1 | | 10/2001 | Custer et al. |
| 6,402,702 B1 | | 6/2002 | Gilcher et al. |
| 6,491,656 B1 | * | 12/2002 | Morris ................ A61M 1/3621 210/257.2 |
| 7,198,751 B2 | | 4/2007 | Carpenter et al. |
| 7,566,315 B2 | | 7/2009 | Hirabuki |
| 7,682,563 B2 | | 3/2010 | Carpenter et al. |
| 7,686,779 B1 | | 3/2010 | Gibbs |
| 7,842,001 B2 | | 11/2010 | Masaoka et al. |
| 8,029,454 B2 | | 10/2011 | Kelly et al. |
| 8,343,085 B2 | | 1/2013 | Toyoda et al. |

(Continued)

FOREIGN PATENT DOCUMENTS

EP        0959980 B2    2/2012

*Primary Examiner* — Leslie Deak
(74) *Attorney, Agent, or Firm* — Cook Alex Ltd.

(57) ABSTRACT

Methods and systems for priming biological fluid processing systems are disclosed. In accordance with such methods and systems, the disposable fluid processing circuit is primed by introducing a first priming solution into a portion of the circuit and a second priming solution into a portion of the circuit. The amount of citrate returned to the biological flood source is minimized.

24 Claims, 10 Drawing Sheets

(56) References Cited

U.S. PATENT DOCUMENTS

| | | | |
|---|---|---|---|
| 8,449,488 B2 | 5/2013 | Hirabuki | |
| 8,834,402 B2 | 9/2014 | Pages et al. | |
| 8,834,403 B2 | 9/2014 | Kelly et al. | |
| 8,877,063 B2 | 11/2014 | Kawarabata et al. | |
| RE45,315 E | 12/2014 | Gilcher et al. | |
| 8,932,469 B2 | 1/2015 | Childers et al. | |
| 8,980,094 B2 | 3/2015 | Fischer et al. | |
| 2007/0062861 A1* | 3/2007 | Lannoy | A61M 1/342 210/501 |
| 2007/0118063 A1 | 5/2007 | Gibbs | |
| 2012/0193290 A1* | 8/2012 | Breuel | A61M 1/16 210/646 |
| 2014/0069868 A1* | 3/2014 | Nguyen | A61M 1/3643 210/650 |
| 2014/0100507 A1* | 4/2014 | Flexman | A61M 1/3643 604/6.05 |
| 2014/0190887 A1 | 7/2014 | Rhode et al. | |

\* cited by examiner

METHODS AND SYSTEMS FOR PRIMING A BIOLOGICAL FLUID PROCESSING CIRCUIT

FIELD OF THE DISCLOSURE

The present disclosure is directed to methods and systems for processing a biological fluid, such as but not limited to blood. More particularly, the present disclosure is directed to methods and systems for priming a biological fluid processing circuit. Even more particularly, the present disclosure is directed to methods and systems for priming a biological fluid processing circuit in a way that limits or otherwise minimizes the amount of citrate that may be returned to a donor.

BACKGROUND

Various blood processing systems now make it possible to collect and/or process particular blood constituents, instead of whole blood, from a blood source such as, but not limited to, a container of previously collected blood or other living or non-living source. Typically, in such systems, whole blood is drawn from a blood source, a particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into one or more of its constituents (e.g., red cells, platelets, and plasma) by processing through a disposable fluid processing circuit that is associated with a durable, reusable device that controls the processing of fluid through the flow circuit by a variety of pumps, clamps or valves, sensors and the like that operate on the fluid flow circuit. Typical separation techniques include centrifugation, such as in the AMICUS® separator from Fenwal, Inc. of Lake Zurich, Ill., or other centrifugal separation devices, or membrane separation such as a spinning membrane-type separator, such as the AUTOPHERESIS-C® and AURORA® devices from Fenwal, Inc. Systems and the separators of such systems that utilize a spinning membrane are also described in WO 2012/125457, the contents of which are incorporated herein by reference.

While the above refers to apheresis systems in particular, the present subject matter, as seen below is not limited to such whole blood apheresis applications but may include systems for processing blood components or other biological fluid components. With reference to apheresis systems, as noted above, blood components that are not collected are typically returned to the patient or donor. These may include concentrated red cells, plasma, platelets or some combination of these. Also, it is not uncommon to infuse into the donor or patient a replacement fluid, such as saline, to replace the volume of the blood components that have been removed and not returned. To this end, such systems include a fluid flow path that communicates with the source or subject, such as but not limited to a human donor or patient, for directing or returning blood, blood components or other fluids to the subject. The fluid flow path is usually in the form of flexible plastic flow tubing terminating in a needle or other access device that is inserted into a subject's (human donor's or patient's) vein.

Prior to the separation of the biological fluid and collection of the desired components, the fluid processing circuit is typically "primed" with one or more solutions and/or optionally blood. Priming the circuit prior to biological fluid (e.g., blood) processing assists in purging air from the system in order to prevent the hemolysis of the red blood cells. Priming also wets the surfaces of the processing unit or separator that will be contacted by the biological fluid. For example, where the processing unit utilizes a membrane such as in the aforementioned AUTOPHERESIS-C® and AURORA® devices, priming coats the surface of the membrane thereby increasing the useable membrane surface and maximizing separation efficiency.

The fluid processing circuit may be primed by introducing a volume of a solution commonly used in the processing of a biological fluid such as anticoagulant and/or saline. In addition, the systems may also be primed with blood from the donor. The use of an anticoagulant as a priming solution is not uncommon in biological fluid processing and blood processing, in particular. Saline, which is also sometimes used in biological fluid processing protocols may also be used to prime the circuit. Anticoagulants that find use in the processing of blood such as acid-citrate-dextrose or anticoagulant citrate dextrose (generally referred to as ACD but also including versions thereof such as ACD-A and ACD-B), citrate-phosphate-dextrose (generally referred to as CPD, but also including versions or variants thereof such as CPDA, CPDA-1 and CPD-50), or sodium citrate include an amount of citrate ion. While citrate is effective in preventing the coagulation of blood it can cause adverse reactions in a human donor or patient when infused at a high rate and/or concentration. Such citrate reactions may cause chills, tingling in the lips or even seizures and convulsions.

Thus, the amount of citrate, including the citrate used to prime the circuit must be controlled. Particular attention to the infusion of citrate must be paid in those systems where the total volume of the flow circuit and/or size of the separation area (e.g., membrane surface) are large, thereby requiring more priming solution. The methods and systems disclosed herein address the challenges posed by such systems.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto. These and other aspects may be found in the description, drawings, claims and the additional listing of various aspects set forth later in this specification.

In one aspect, the present disclosure is directed to a method of priming a biological fluid processing circuit including mounting a biological fluid processing circuit that includes a biological fluid processor, a reservoir, one or more containers of processing solutions, a biological fluid access device and a flow path establishing flow communication between said one or more solutions and a source of biological fluid, the processor and the reservoir onto a hardware component of a biological fluid processing system in a predetermined relationship. The method also includes selecting a biological fluid processing protocol, introducing a selected amount of a first solution from a first container of a processing solution to a selected point in the flow path, and introducing a biological fluid from said source into said flow path.

In another aspect, the present disclosure is directed to a fluid processing system including a disposable fluid processing circuit comprising a fluid processing device, a reservoir, access devices for establishing fluid communication with one or more containers of a processing fluid, a reservoir, an access device for establishing fluid communication with a biological fluid source and tubing for establishing flow communication between processing device, reservoir, said one or more containers, and the fluid source. The system also includes a reusable hardware unit for receiving the fluid processing circuit in a predetermined relationship, and a controller with pre-programmed instructions for carrying out a selected fluid processing protocol and for priming the circuit according to the protocol selected.

DETAILED DESCRIPTION OF THE EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

Figure 1:
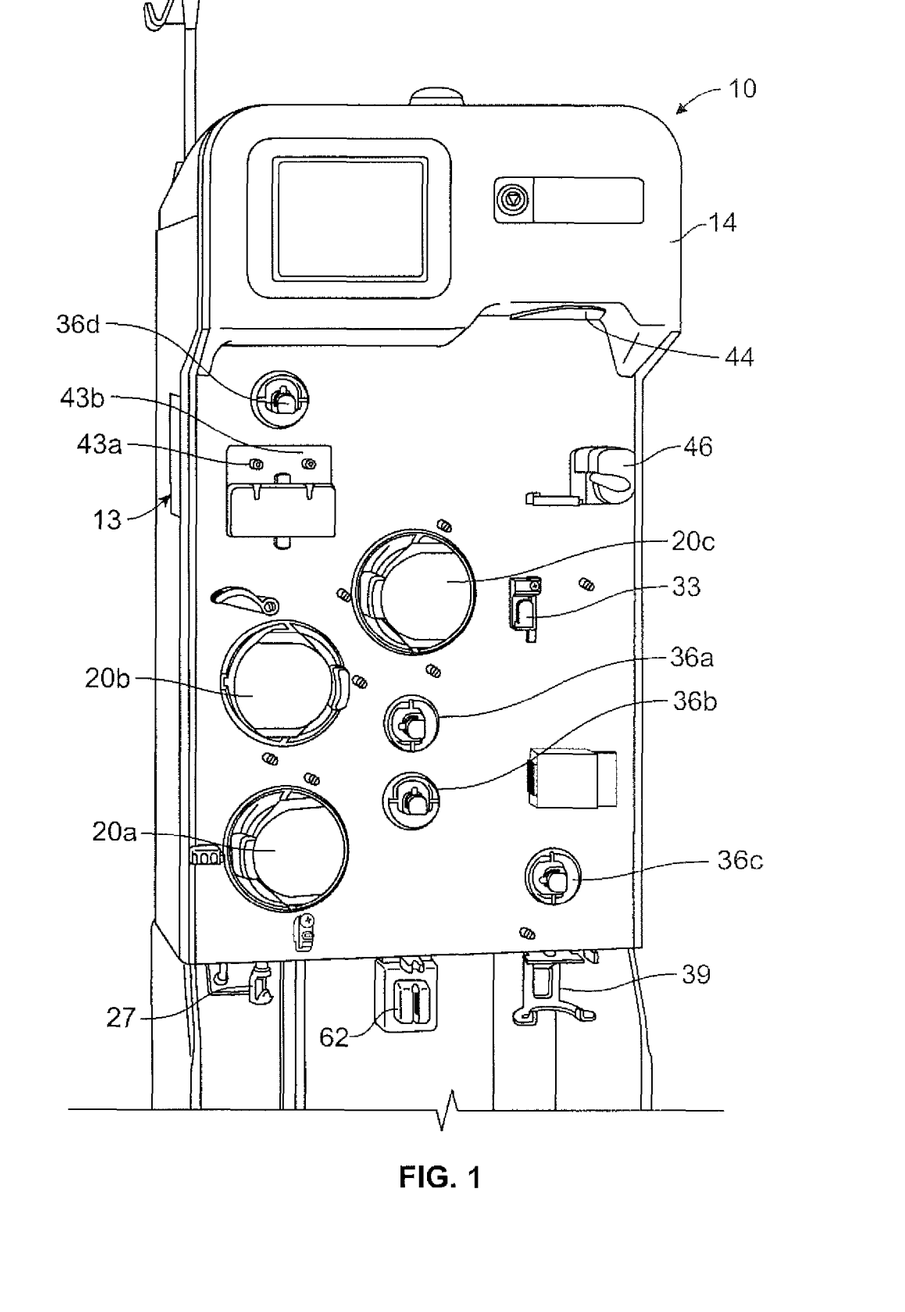
FIG. 1 is a front perspective view of an exemplary fluid separation system according to an aspect of the present disclosure.
Figure 2:
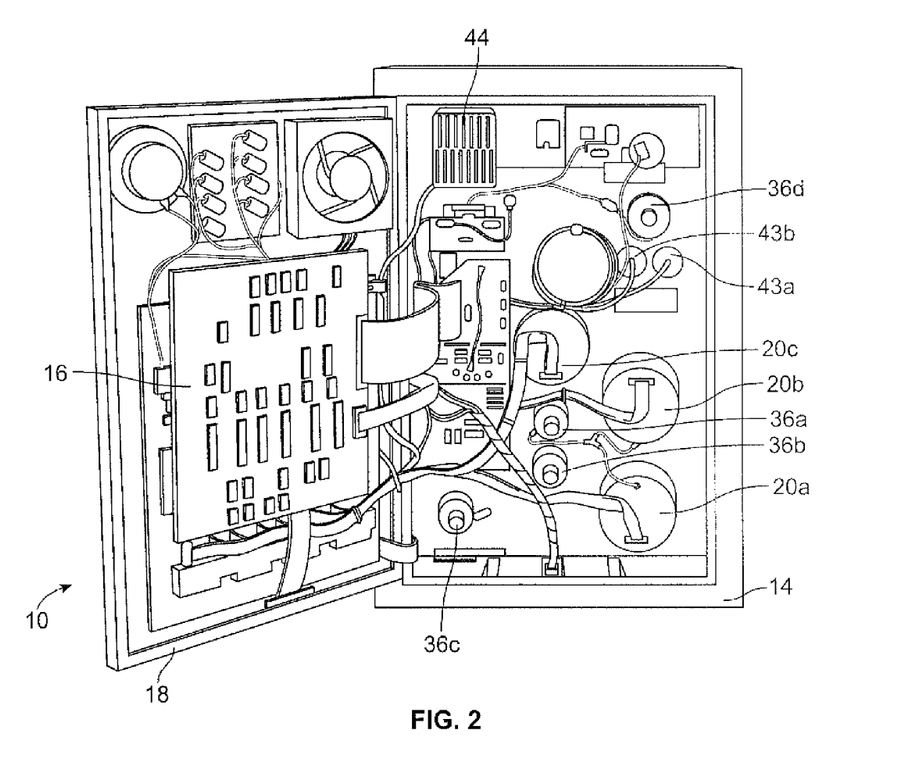
FIG. 2 is a rear perspective view of the fluid separation system of FIG. 1, with a rear door thereof in an open position.
Figure 3:
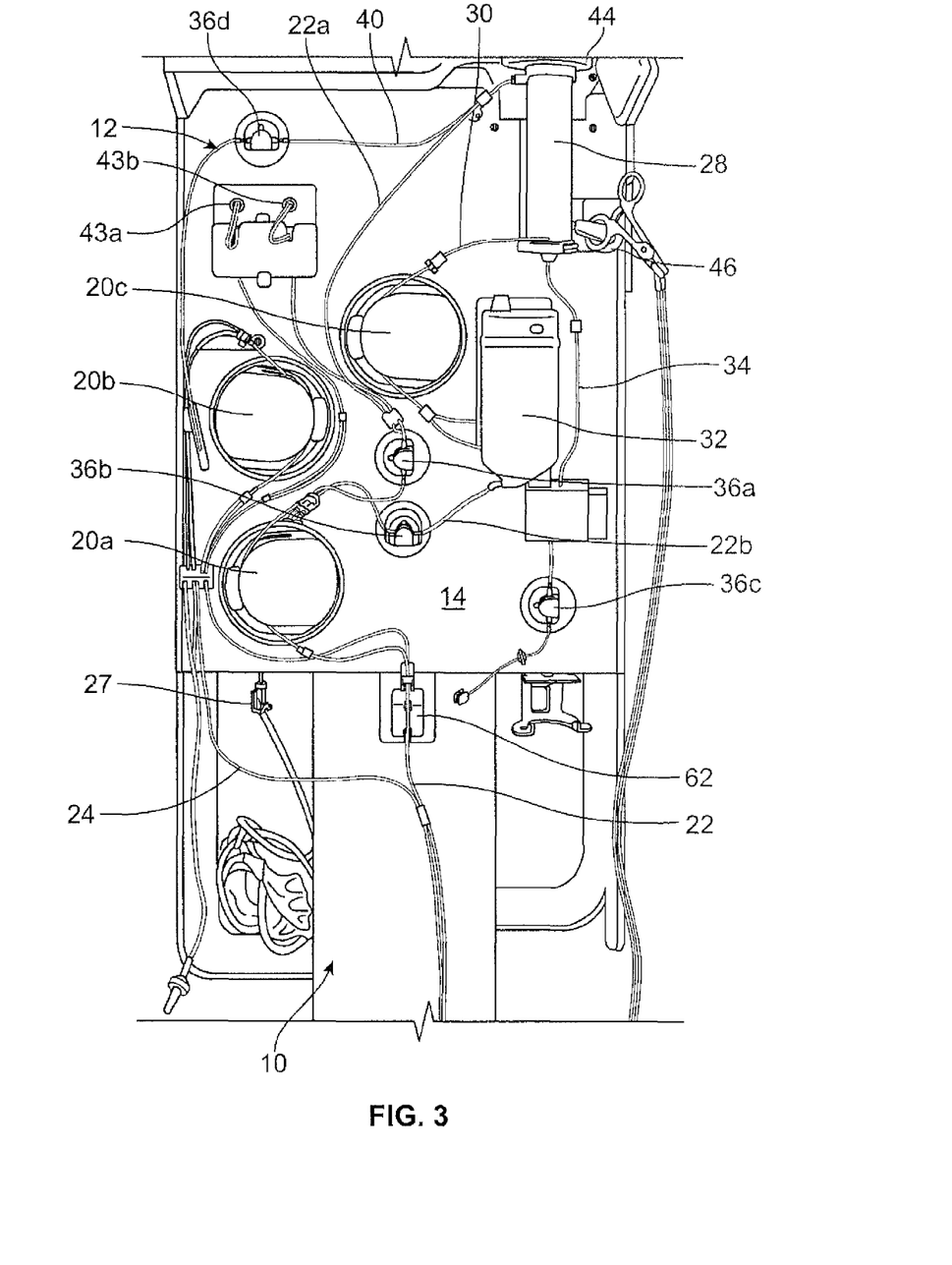
FIG. 3 is a front perspective view of the fluid separation system of FIG. 1, with a fluid processing circuit associated therewith.

The present disclosure is directed to methods and systems for processing a biological fluid such as, but not limited to, blood. According to an aspect of the present disclosure, a durable or reusable hardware unit in combination with a separate fluid processing circuit (which may be disposable) to separate a plasma-containing fluid into separated plasma and a concentrated fluid. FIGS. 1 and 2 illustrate an exemplary fluid separation system 10, while FIG. 3 illustrates an exemplary fluid flow circuit 12 mounted onto the hardware unit 13, but it should be understood that the illustrated fluid separation system 10 and fluid processing circuit 12 are merely exemplary of such systems and circuits and that differently configured fluid processing systems and fluid flow circuits may be provided without departing from the scope of the present disclosure.

The system 10 of FIG. 1 is configured for processing whole blood, but it may be used to process any other plasma-containing fluid to separate plasma from concentrated fluid (which may be red cell concentrate or packed red cells when the plasma-containing fluid constitutes whole blood). The plasma-containing fluid may come from any fluid source, which may include a living donor or patient (e.g., a human blood donor) or a non-living source (e.g., a blood bag or fluid container).

Figure 5:
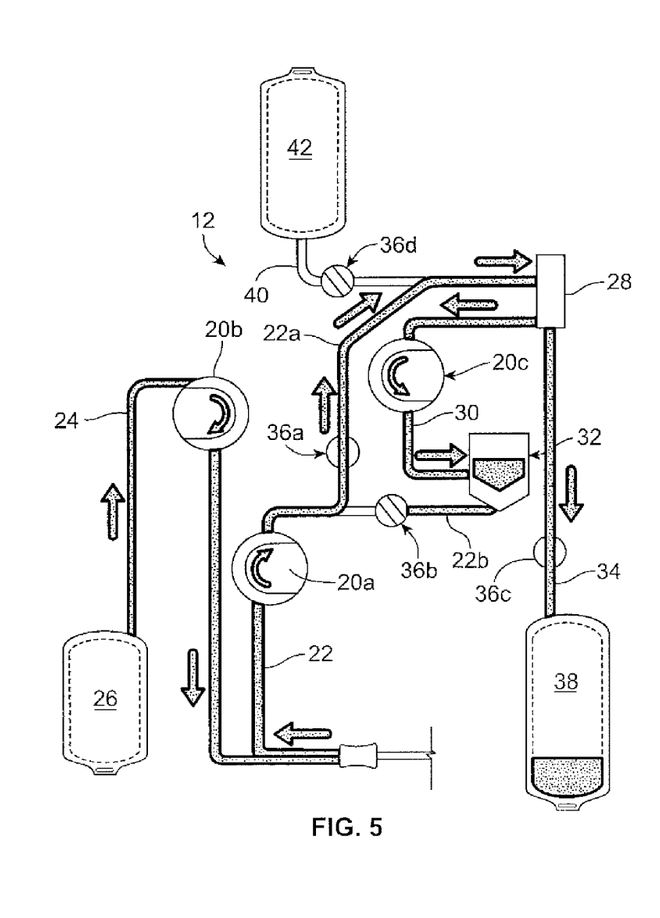
FIG. 5 is a schematic view of the fluid processing circuit and fluid separation system of FIG. 3, in a fluid draw mode.
Figure 6:
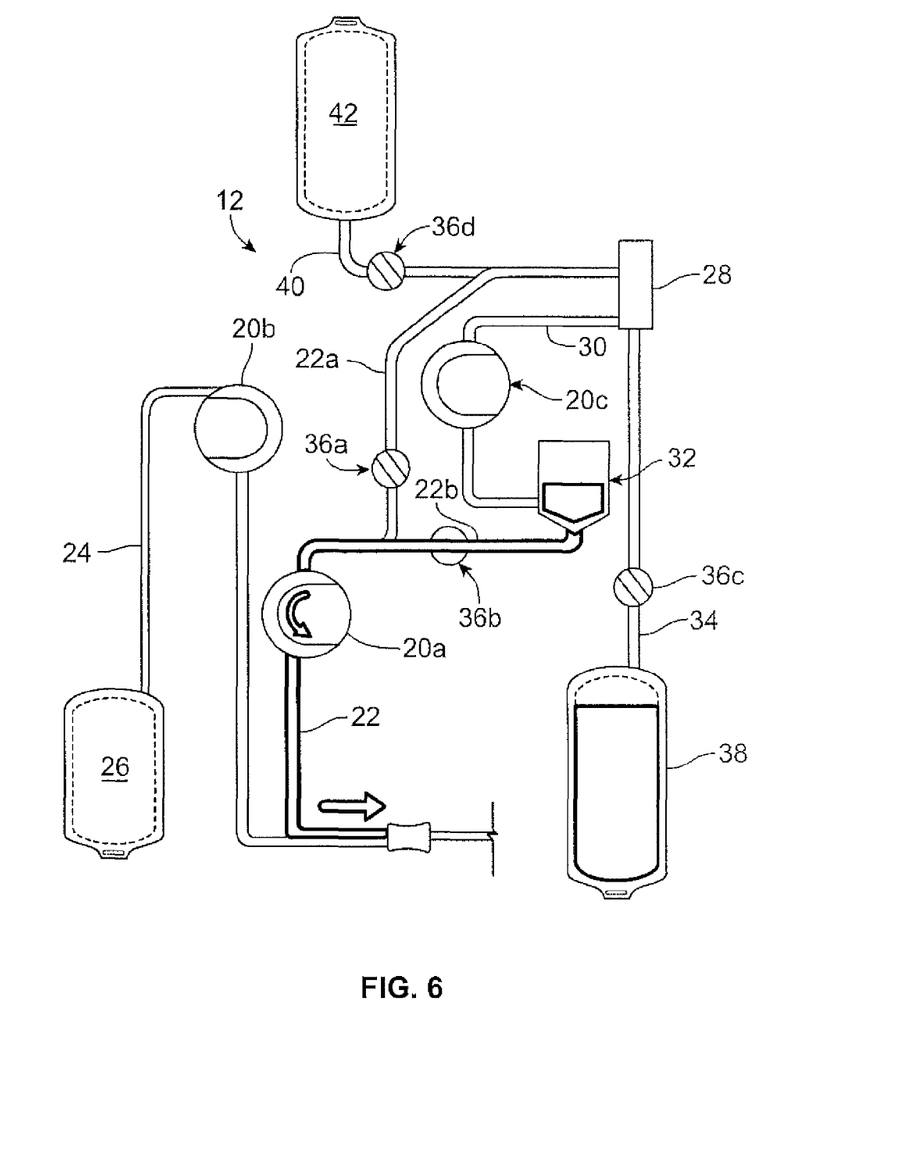
FIG. 6 is a schematic view of the fluid processing circuit and fluid separation system of FIG. 3, in a fluid return mode.

The illustrated system 10 includes the hardware unit 13 shown as a cabinet or housing 14, with several components positioned outside of the cabinet 14 (e.g., associated with a front wall or surface or panel of the cabinet 14) and additional components (including a central processing unit or controller 16) and interconnects positioned inside of the cabinet 14, which may be accessed by opening a rear door 18 of the system 10, as shown in FIG. 2. "Controller" is used generally and may include any higher or lower level processors that are part of the overall control or operation of the system or process, whether combined in a single processing unit or separate discrete components or structures. Among the system components positioned on the outside of the cabinet 14, one or more pumps or pump stations 20a-20c may be provided, with the pumps 20a-20c configured to accommodate tubing lines of the fluid flow circuit 12. One of the pumps 20a may be provided as a source/recipient access pump, which may be associated with a source/recipient access line 22 of the fluid flow circuit 12 and operates to draw fluid from a fluid source (FIG. 5) and to return fluid from the concentrated fluid reservoir 32 to a fluid recipient (FIG. 6). Another one of the pumps 20b may be provided as an anticoagulant pump, which may be associated with an anticoagulant line 24 of the fluid flow circuit 12 and operates to add anticoagulant from an anticoagulant source or container 26 of the fluid flow circuit 12 (FIG. 5) to fluid drawn from the fluid source in the source/recipient access line 22 before the fluid enters into a fluid separation module or chamber 28 of the fluid flow circuit 12. A third pump 20c may be provided as a concentrated fluid pump, which may be associated with a concentrated fluid outlet line 30 and operates to draw concentrated fluid from the fluid separation chamber 28 and direct it into a concentrated fluid reservoir 32 after the plasma-containing fluid has been separated into a concentrated fluid and separated plasma in the fluid separation chamber 28. Pump 20a may pump concentrated fluid from reservoir 32 back to the donor.

In the illustrated embodiment, the pumps 20a-20c are peristaltic pumps, but it is within the scope of the present disclosure for differently configured pumps, such as diaphragm or other pumps, to be provided. Furthermore, additional or alternative pumps may be provided without departing from the scope of the present disclosure. For example, a pump may be associated with a plasma outlet line 34 of the fluid processing circuit 12 to draw separated plasma from the fluid separation chamber or separator 28 after the plasma-containing fluid has been separated into a concentrated fluid and separated plasma. Also, as will be described in greater detail herein, the illustrated embodiment employs a single fluid flow tubing or flow path for both drawing fluid from a source and flowing or returning it to a recipient, which are carried out intermittently. The system 10 could employ separate draw and return flow paths or tubes without departing from the scope of the present disclosure.

In addition to the pumps 20a-20c, the external components of the system 10 may include one or more clamps or valves 36a-36d associated with the tubing lines of the fluid processing circuit 12. The clamps or valves 36a-36d may be variously configured and operate to selectively allow and prevent fluid flow through the associated tubing line. In the illustrated embodiment, one clamp or valve 36a may be provided as a fluid source/recipient clamp or valve, which may be associated with a draw branch 22a of the source/recipient access line 22 of the fluid flow circuit 12 to allow (FIG. 5) or prevent (FIG. 6) the flow of fluid through the draw branch 22a of the source/recipient access line 22. Another one of the clamps or valves 36b may be provided as a reinfusion clamp or valve, which may be associated with a reinfusion branch 22b of the source/recipient access line 22 downstream of a concentrated fluid reservoir 32 of the fluid flow circuit 12 to allow (FIG. 6) or prevent (FIG. 5) the flow of concentrated fluid through the reinfusion branch 22b. A third clamp or valve 36c may be provided as a plasma clamp or valve, which may be associated with the plasma outlet line 34 to allow (FIG. 5) or prevent (FIG. 6) the flow of separated plasma through the plasma outlet line 34 and into a separated plasma container 38. A fourth clamp or valve 36d may be provided as a replacement fluid clamp or valve, which may be associated with a replacement fluid line 40 of the fluid flow circuit 12 to allow or prevent the flow of a replacement fluid out of a replacement fluid source 42 (e.g., a bag or container at least partially filled with saline). Additional or alternative clamps or valves may also be provided without departing from the scope of the present disclosure.

The illustrated system 10 further includes one or more pressure sensors 43a and 43b that may be associated with the fluid flow circuit 12 to monitor the pressure within one or more of the tubing lines of the fluid flow circuit 12 during operation of the pumps 20a-20c and clamps or valves 36a-36d. In one embodiment, one pressure sensor 43a may be associated with a tubing line that draws fluid from a fluid source and/or directs processed fluid to a fluid recipient, while the other pressure sensor 43b may be associated with a tubing line that directs fluid into or out of the fluid separation chamber 28 to assess the pressure within the fluid separation chamber 28, but the pressure sensors 43a and 43b may also be associated with other tubing lines without departing from the scope of the present disclosure. The pressure sensors 43a and 43b may send signals to the system controller that are indicative of the pressure within the tubing line or lines being monitored by the pressure sensor 43a, 43b. If the controller determines that an improper pressure is present within the fluid flow circuit 12 (e.g., a high pressure due to an occlusion of one of the tubing lines), then the controller may instruct one or more of the pumps 20a-20c and/or one or more of the clamps or valves 36a-36d to act so as to alleviate the improper pressure condition (e.g., by reversing the direction of operation of one of the pumps 20a-20c and/or opening or closing one of the clamps or valves 36a-36d). Additional or alternative pressure sensors may also be provided without departing from the scope of the present disclosure.

As shown in FIG. 1, the system 10, and more specifically, hardware unit 13 may also include a separation actuator 44 that interacts with a portion of the fluid separation chamber 28 to operate the fluid separation chamber or separator 28 of the fluid processing circuit 12 (FIG. 3). A chamber lock 46 may also be provided to hold the fluid separation chamber 28 in place with respect to the system cabinet 14 and in engagement with the separation actuator 44. The configuration and operation of the separation actuator 44 depends upon the configuration of the fluid separation chamber 28. In the illustrated embodiment, the fluid separation chamber 28 is provided as a spinning membrane-type separator, such as a separator of the type described in greater detail in U.S. Pat. Nos. 5,194,145 and 5,234,608 or in PCT Patent Application Publication No. WO 2012/125457 A1, all of which are hereby incorporated herein by reference. If provided as a spinning membrane-type separator, the fluid separation chamber 28 may include a tubular housing 48 (FIG. 4), with a microporous membrane 50 positioned therein. An inlet 52 allows a plasma-containing fluid to enter into the housing 48 (via the draw branch 22a of the source/recipient access line 22), while a side outlet 54 allows concentrated fluid to exit the housing 48 (via the concentrated fluid outlet line 30) and a bottom outlet 56 allows separated plasma to exit the housing 48 (via the plasma outlet line 34) after the plasma-containing fluid has been separated into concentrated fluid and plasma.

Figure 4:
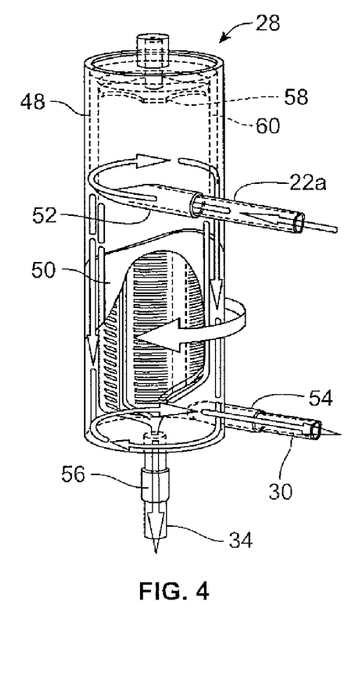
FIG. 4 is a front perspective view of a fluid separator of the fluid processing circuit of FIG. 3, with a portion thereof broken away for illustrative purposes.

In the illustrated embodiment, as seen in FIG. 4, the separation actuator 44 is provided as a driver that is magnetically coupled to a rotor 58 on which the membrane 50 is mounted, with the separation actuator 44 causing the rotor 58 and membrane 50 to rotate about the central axis of the housing 48. The rotating rotor 58 and membrane 50 create Taylor vortices within a gap 60 between the housing 48 and the membrane 50, which tend to transport the concentrated fluid (which may be cellular blood components) away from the membrane 50 to exit the fluid separation chamber 28 via the side outlet 54, while the separated plasma passes through the membrane 50 toward the central axis of the housing 48 to exit the fluid separation chamber 28 via the bottom outlet 56. It should be understood that the present disclosure is not limited to a particular fluid separation chamber and that the illustrated and described fluid separation chamber 28 is merely exemplary. For example, in other embodiments, a centrifugal device that separates fluid components based on density, rather than size, may be employed to separate a plasma-containing fluid into plasma and a concentrated fluid.

The system 10 may further includes a hemoglobin detector or optical sensor assembly 62 associated with the plasma outlet line 34 when the fluid flow circuit 12 has been installed on the system 10. The optical sensor assembly 62 is used to determine the concentration of hemoglobin in the separated plasma flowing through the plasma outlet line 34 (and may also detect other irregularities in the plasma outlet line 34, such as red blood cells, lipids, and air bubbles) and may be variously configured.

System 10 may further include air detector 62 shown in FIGS. 1 and 3. Air detector 62 receives donor line 22 (which is connected to the donor or other source of biological fluid) and detects the presence of air or fluid in the donor line.

The illustrated membrane material may be formed into a sheet or film using any suitable techniques to define the membrane 50 that is to be mounted onto the rotor 58 of the fluid separation chamber 28. The dimensions and configuration of the membrane 50 may vary without departing from the scope of the present disclosure, but in one embodiment a membrane 50 such as described above, and used for separation of whole blood into plasma and cellular components may have a thickness in the range of approximately 5 μm to approximately 1000 μm (preferably in the range of approximately 25 μm to approximately 200 μm), with a mean pore size in the range of approximately 0.2 μm to approximately 200 (preferably in the range of approximately 0.5 μm to approximately 10 μm and more preferably in the range of approximately 0.6 μm to approximately 5 μm). The porosity of the membrane 50 may also vary, such as from approximately 1% to approximately 90%, but preferably in the range of approximately 50% to approximately 80% to produce a membrane 50 that passes fluid therethrough at a relatively high rate while being sufficiently strong to withstand the forces applied to it by the spinning rotor 58 and fluid contact during a separation procedure.

According to one method of using the fluid separation system 10 and fluid flow circuit 12, a fluid is drawn from a fluid source into the fluid separation chamber 28, or a temporary holding chamber, during a draw phase or mode (FIG. 5), where it is separated into return fluid (e.g., cellular blood components) and collection fluid (e.g., substantially cell-free plasma). The collection fluid is retained by the system 10, while the return fluid is temporarily retained and returned to the fluid source during a return or infusion phase or mode (FIG. 6).

Figure 7:
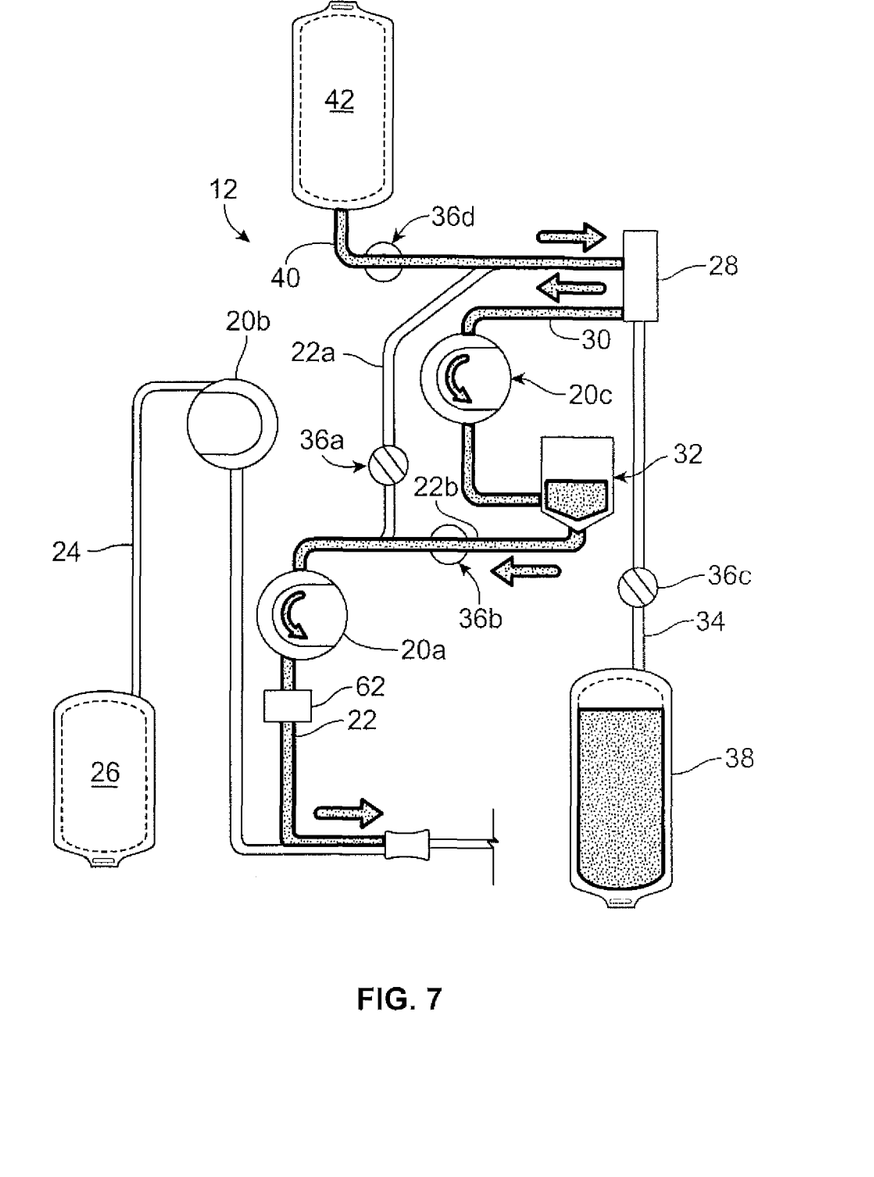
FIG. 7 is a schematic view of the fluid flow circuit and fluid separation system of FIG. 3, in a fluid return mode in which the return fluid is a replacement fluid, such a s saline.

FIG. 7 shows an exemplary phase or mode in which replacement fluid (e.g., saline) is directed to the fluid recipient, either alone or with an amount of return/processed fluid. In the phase of FIG. 7, the clamp or valve 36d associated with the replacement fluid line 40 is opened to allow replacement fluid to flow out of the replacement fluid source 42. The clamp or valve 36a associated with the draw branch 22a of the source/recipient access line 22 may be in a closed condition to prevent fluid flow therethrough, such that the replacement fluid is directed into the fluid separation chamber 28. The replacement fluid is pulled out of the fluid separation chamber 28 and into the return fluid reservoir 32 by operation of the pump 20c associated with the return fluid outlet line 30. If there is any return fluid in the return fluid reservoir 32, then the replacement fluid mixes with the return fluid prior to being pumped to the fluid recipient by the pump 20a associated with the fluid recipient line 22, otherwise the replacement fluid alone may be pumped to the fluid recipient. In one embodiment, the replacement fluid return mode of FIG. 7 is carried out only once, as a final return phase (e.g., when the amount of return fluid in the return fluid reservoir 32 is at a sufficiently low level) in which a mixture of return fluid and replacement fluid is returned to the fluid recipient. This may be advantageous to ensure that all of the return fluid in the return fluid reservoir 32 (along with any remaining in the fluid separation chamber 28) is rinsed out of the return fluid reservoir 32 and pumped to the fluid recipient.

In other embodiments, the replacement fluid return mode of FIG. 7 may be carried out at other times, such as earlier in the procedure, at multiple scheduled times during a procedure, and/or at any time upon a request from the operator and/or using a different path between the replacement fluid source 42 and the fluid recipient. For example, it may be advantageous for the replacement fluid to bypass the fluid separation chamber and the return fluid reservoir 32 if the replacement fluid is being pumped to a fluid recipient earlier in the procedure. In this case, the clamp or valve 36d associated with the replacement fluid line 40 and the clamp or valve 36a associated with the draw branch 22a of the source/recipient access line 22 may be opened to allow fluid flow therethrough, with the clamp or valve 36b associated with the reinfusion branch 22b in a closed condition to prevent fluid flow therethrough. The pump 20a associated with the fluid recipient line 22 may be activated (with the other two pumps 20b and 20c inactive) to draw replacement fluid out of the replacement fluid source 42 and through the replacement fluid line 40, the draw branch 22a, and finally the source/recipient access line 22 to the fluid recipient.

In one embodiment, the draw and return phases are repeatedly alternated (drawing from the fluid source, separating the fluid from the fluid source into return fluid and collection fluid, and then pumping the return fluid and/or a replacement fluid to the fluid source or a different recipient) until a target (e.g., a particular amount of collection fluid) is achieved. All of the draw phases and all of the return phases may be identical to or may differ from each other. For example, a final draw phase may draw less fluid from the fluid source than the previous draw phases and a final return phase may infuse a combination of return fluid and replacement fluid to the fluid recipient, whereas the previous return phases pump might only return fluid to the fluid recipient.

Turning now to the methods of priming the systems described above prior to the separation and collection of blood and blood components, the priming sequence and the solutions used to prime the processing circuit 12 and the volumes thereof may depend, at least in part, on the processing protocol selected by the operator. The protocols may use one or two "non-blood" solutions and/or blood as the priming solutions. The non-blood solutions may include anticoagulant, saline, or other biological fluid. In one embodiment, anticoagulant may be used to prime a portion of processing circuit 12, while blood may be used to prime a different portion of processing circuit 12. In another embodiment, anticoagulant may be used to prime a portion of the fluid processing circuit 12, while saline or other replacement fluid may be used to prime a different portion of fluid processing circuit 12. In either case, blood from the donor or source may be introduced following the introduction of anticoagulant and/or replacement fluid to further prime the system, as will be described in greater detail below.

Figure 8:
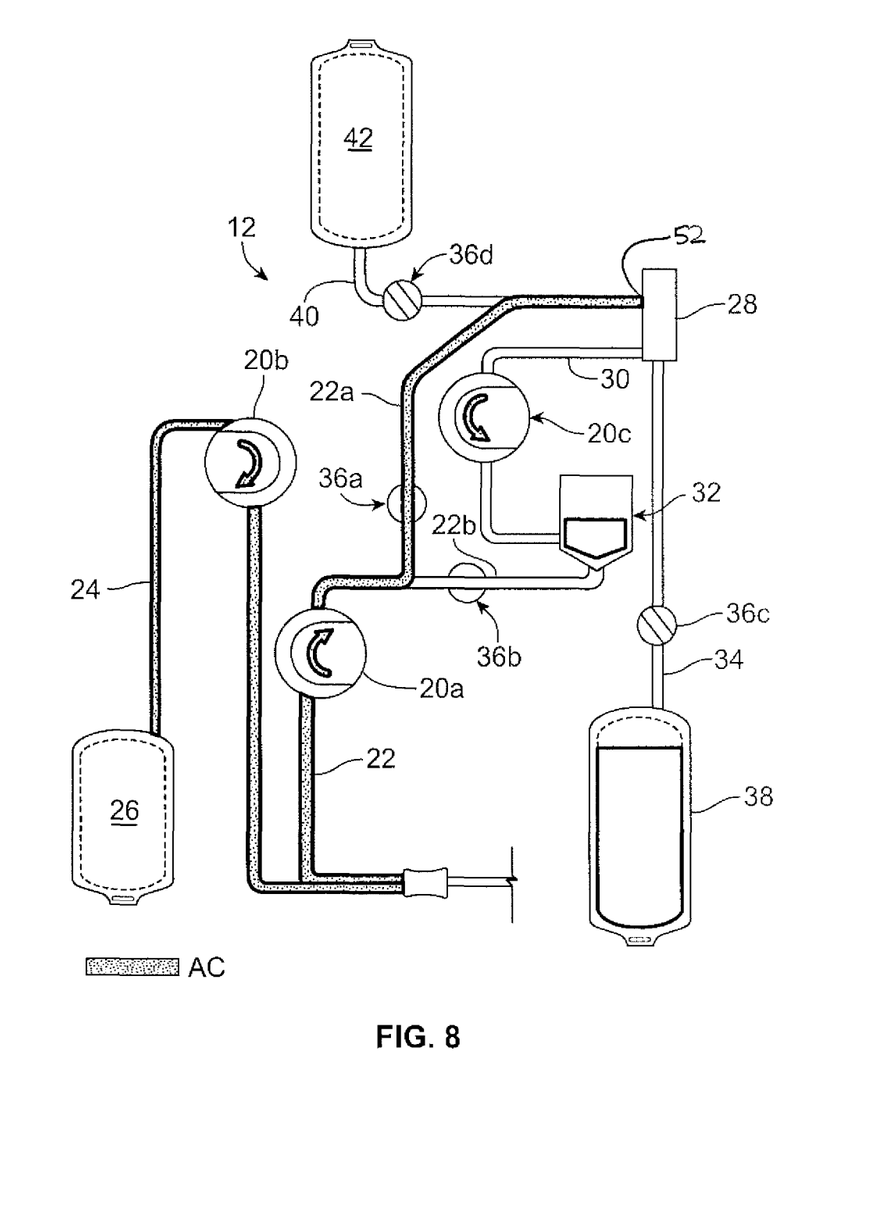
FIG. 8 is a schematic view of the fluid processing circuit and fluid separation system of FIG. 3 showing the path of a first priming a solution in a selected processing protocol.

Protocols may be characterized as either a "non-saline" protocol where no replacement fluid is used or a "saline" protocol where some replacement fluid, such as saline, is delivered to the donor/patient. As described in greater detail below, in both protocols anticoagulant is pumped but to different points in the circuit 12. Thus, in a first step, after the disposable fluid circuit 12 has been mounted onto hardware unit 13 (e.g., cabinet 14), the operator selects the desired protocol, i.e., a non-saline protocol or a saline protocol. Where a non-saline protocol is selected, anticoagulant is first drawn from anticoagulant container 26 by the action of peristaltic pump 20b (FIG. 8), under the direction of the controller. The anticoagulant used may be any one of the citrate based anticoagulants described above or may be a non-citrate anticoagulant such as heparin. As pump 20b is drawing anticoagulant from container 26, pumps 20a and 20c may likewise be moving (rotating) simultaneously to keep fluid moving in the desired direction. As anticoagulant is being withdrawn from container 26, clamp or valve 36a is open, clamp or valve 36b may be open, and clamps or valves 36c and 36d are closed to direct fluid (anticoagulant) toward the inlet of separator as shown in FIG. 8. In one embodiment, pump rates for pumps 20b, 20a and 20c are approximately equal. To minimize the volume of citrate that is later introduced back to the donor/patient, the amount of anticoagulant introduced is less than the entire volume of at least fluid flow circuit 12 and the area or volume of processing device 28.

With reference to FIG. 8, in one example, anticoagulant may be introduced from container 26 through flow path anticoagulant line 24 where it joins with donor line 22, up to the inlet port 52 of separator 28. Depending on the volume capacity of fluid circuit 12 and the volume of the separator, the point to which anticoagulant is introduced may be elsewhere in the fluid processing circuit. For example, in fluid processing circuits of lesser volume capacity (and membranes of smaller surface area), the point to which anticoagulant is delivered during priming may be upstream of separator 28. In accordance with the present disclosure, the volume of anticoagulant delivered to fluid circuit 12 may be determined by one or more monitors or indicators of system 10. In one embodiment during initial priming with anticoagulant, as liquid is drawn from anticoagulant container 26, air detector 62 detects the presence of liquid in the donor line 22. When liquid, i.e., anticoagulant, is initially detected by air detector 62, a signal is sent to the controller which then directs and actuates pump 20b to pump an additional and predetermined amount of anticoagulant to deliver the anticoagulant to the desired point (e.g., port 52) of processing circuit 12 based on the selected protocol. Additionally, and/or optionally, weight changes in the anticoagulant container 26 may be monitored by a weight scale 27 associated with container 26. Alternatively, the volume of anticoagulant delivered may be monitored by the volume that is displaced by the pump based on pump strokes or rotations. Changes in the weight of container 26 (or the monitoring of the pump strokes) may confirm that the desired amount of anticoagulant has been delivered and, therefore, that the citrate levels that will be reinfused back to the donor/patient are within acceptable limits. In one embodiment, the volume of anticoagulant introduced into flow circuit 12, excluding the amount of anticoagulant in line 24, may be approximately 10-30 ml more particularly approximately 10-20 ml and even more particularly approximately 14 ml in a "non-saline" protocol.

Figure 9:
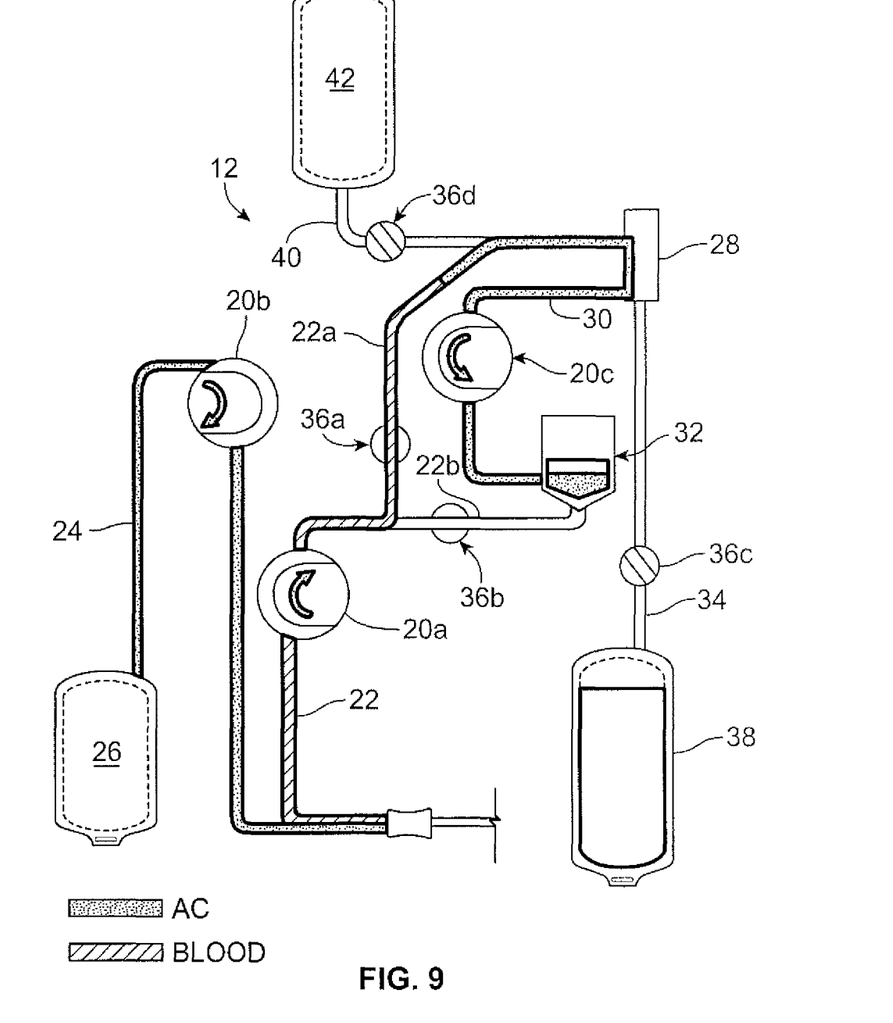
FIG. 9 is a schematic view of the fluid flow circuit and fluid separation system of FIG. 3 showing the path of first and second priming solutions at a later stage of the priming sequence in the selected processing protocol of FIG. 7.

Once primed with anticoagulant, system 10 may be prompted automatically under the direction of the controller and/or by the operator to begin an initial blood draw. Specifically, blood drawn from the donor/patient is drawn through donor line 22. Clamp or valve 36a, as shown in FIG. 9, remains open to allow blood to enter donor line 22. As blood flows into processing circuit, it pushes anticoagulant into separator 28, allowing anticoagulant to wet the membrane of separator 28. Pumps 20a and 20c, under the direction of controller, draw blood from the donor or source and draw anticoagulant fluid from separator 28 and introduce it into reservoir 32.

Figure 10:
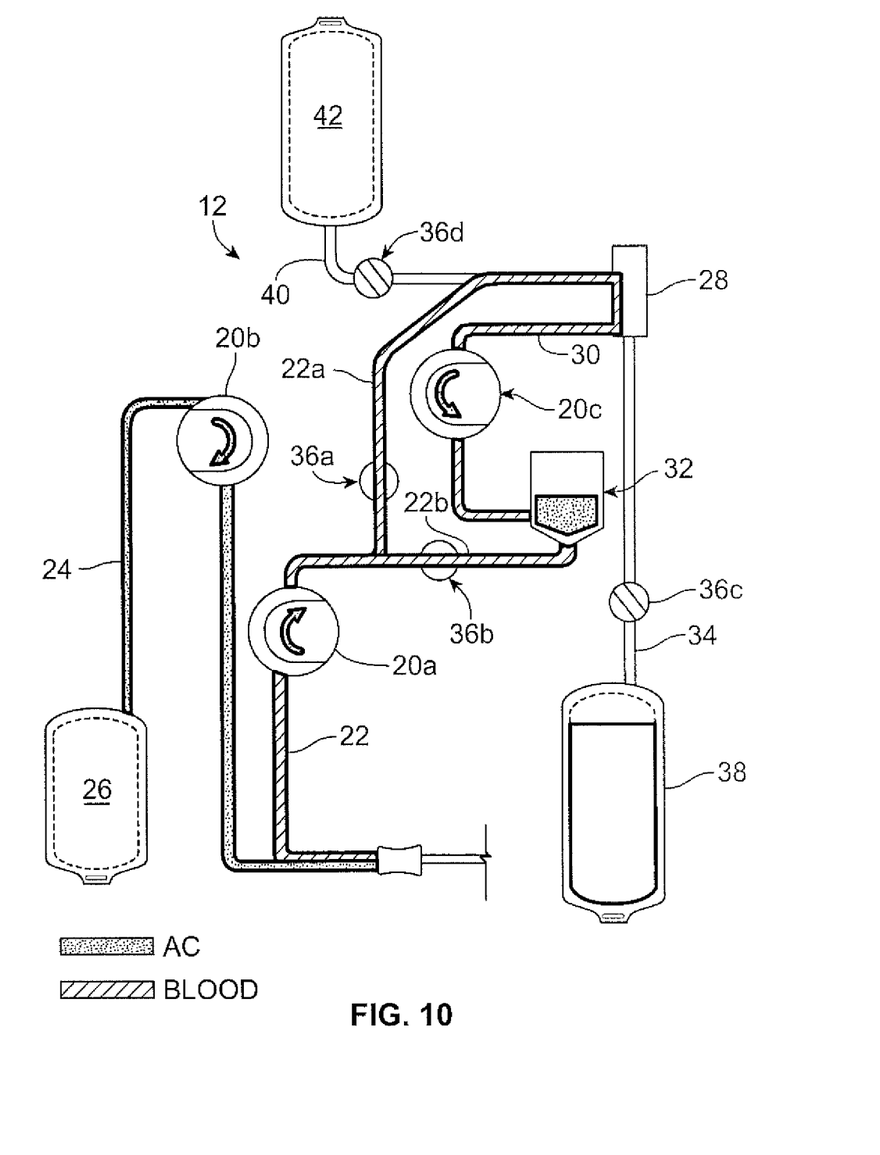
FIG. 10 is a schematic view of the fluid flow circuit and fluid separation system of FIG. 3 showing the path of first and second priming solutions at a still later stage of the priming sequence in the selected processing protocol of FIG. 7.

Continuing with the initial blood draw, pump 20a continues to draw blood from donor or source, and clamp or valve 36b is opened under the direction of controller to allow blood to fill and prime reinfusion line 22b, as shown in FIG. 10. Once circuit 12 has been primed, the non-saline separation/collection protocol may commence.

Figure 11:
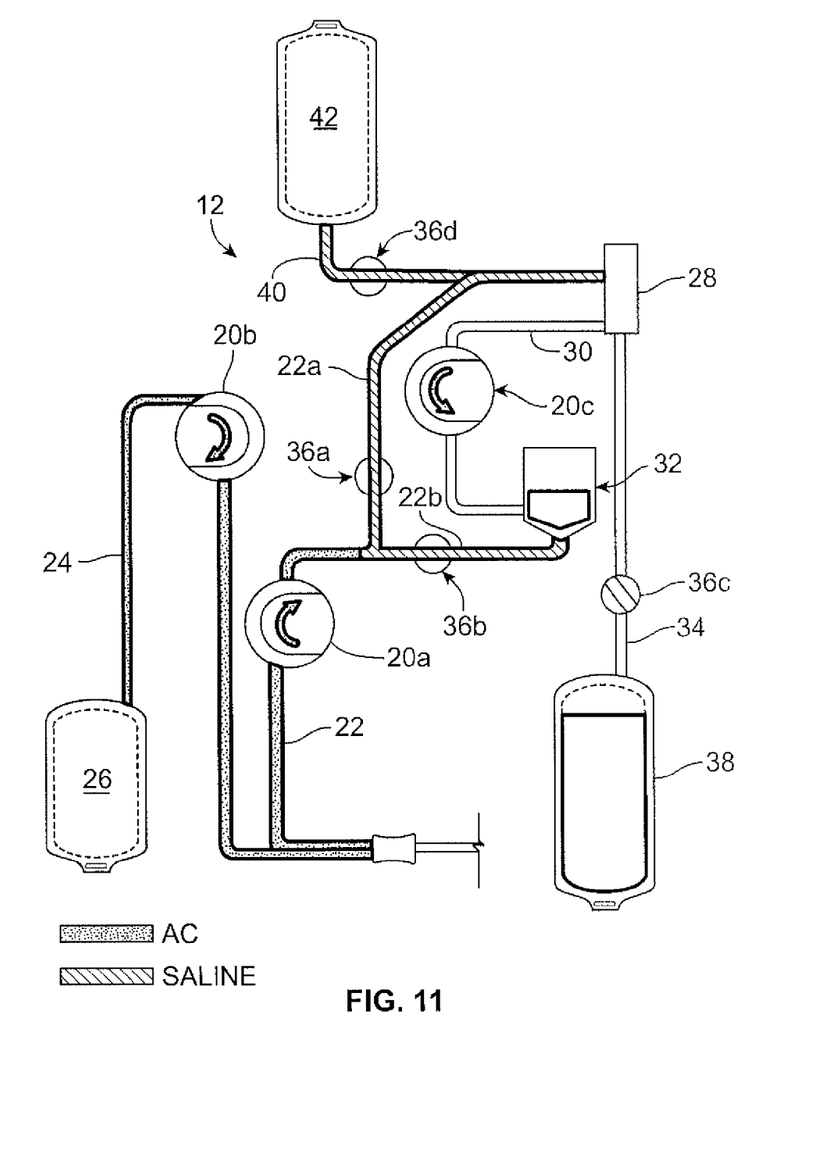
FIG. 11 is a schematic view of the fluid flow circuit and fluid separation system of FIG. 3 showing the path of said first and second priming solutions in a selected and different processing protocol.

A priming sequence for a "saline" protocol is shown in FIG. 11. As noted above, in a saline protocol, circuit 12 may be primed, in part, by anticoagulant and also by a replacement fluid such as saline. Accordingly, in such a protocol, the demand for anticoagulant as the priming solution is lessened. As shown in FIG. 11, anticoagulant is drawn from container 26 and introduced into fluid circuit 12. Also, as described above, once air detector 62 (FIG. 3) detects that there is liquid in donor line 22, the controller instructs additional rotation of anticoagulant pump 20b to deliver anticoagulant to the prescribed point in circuit 12. It will be noted, for example, that inasmuch as part of the system in a saline protocol may be primed by replacement fluid e.g., saline, the point to which anticoagulant is delivered may be well upstream of the endpoint of anticoagulant delivery as described in the non-saline protocol of FIGS. 8-10. Thus, for example, anticoagulant may be delivered to a point just past blood pump 20a, as shown in FIG. 11.

Once air detector 62 has detected the presence of liquid and the anticoagulant weight scale has determined a change in the amount of anticoagulant in the container 26 (or the amount of anticoagulant delivered has been otherwise determined), priming continues with the replacement fluid. Specifically, under the action the controller, clamp or valve 36d is open to allow introduction of replacement fluid, i.e., saline, to enter by, for example, gravity drainage from container 42 to circuit 12. As shown in FIG. 11, saline enters line 22a through open clamp or valve 36a. Following priming with saline, initial blood flow from donor is commenced, which pushes the saline in line 22a and anticoagulant in line 22 into separator 28 to wet the membrane of the separator. The amount of saline or other replacement fluid delivered may be monitored by observing changes in the weight of reservoir 32 as measured by weight scale 33 (FIG. 1). The total volume of saline used may be estimated based on tubing dimensions and the weight added to reservoir 32. Alternatively, as described above in connection with monitoring the volume of delivered anticoagulant, the volume of saline delivered may be monitored by the volume that is displaced by the pump based on pump strokes or rotations. In an embodiment, excluding the anticoagulant line 24, approximately 5-20 ml of anticoagulant and more particularly approximately 10 ml of anticoagulant and approximately 10-25 ml of saline and more particularly approximately 14 ml of saline may be used in the above-described saline protocol.

Other Aspects

In a first aspect, a method of priming a biological fluid processing circuit is provided. The method includes mounting a biological fluid processing circuit that includes a biological fluid processor, a reservoir, one or more containers of processing solutions, a biological fluid access device and a flow path establishing flow communication between said one or more solutions, a source of biological fluid, said processor and said reservoir onto a hardware component of a biological fluid processing system in a predetermined relationship; selecting a biological fluid processing protocol; introducing a selected amount of a first solution from a first container of a processing solution to a selected point in said flow path; and introducing a biological fluid from said source into said flow path.

A second aspect of the present subject matter includes the method in accordance with the first aspect including the step of introducing a selected amount of a second solution from a second container to a selected point in the flow path prior to the step of introducing the biological fluid.

A third aspect of the present subject matter includes the method of the second aspect including the step of introducing the second solution as a result of selecting a biological fluid processing protocol.

A fourth aspect of the present subject matter includes the method of the third aspect wherein the selected biological fluid processing protocol includes delivering a replacement fluid to the biological fluid source.

A fifth aspect of the present subject matter includes the method of any one of the second through fourth aspects wherein said first solution comprises anticoagulant and said second solution comprises a replacement fluid.

A sixth aspect of the present subject matter includes the method of the fifth aspect wherein the replacement fluid is saline.

A seventh aspect of the present subject matter includes the method of any one of the preceding first through sixth aspects wherein said volume of said first solution is between 10 ml and 30 ml.

An eighth aspect of the present subject matter includes the method of the seventh aspect wherein said first solution includes citrate.

A ninth aspect of the present subject matter includes the method of any one of first through eighth aspects including monitoring the volume of the introduced first solution.

A tenth aspect of the present subject matter includes the method of the ninth aspect including monitoring the volume by observing changes in the weight of said first container.

An eleventh aspect of the present subject matter includes the method of the ninth aspect including monitoring the volume by determining the number of pump strokes in a pump associated with said introduced first solution.

In a twelfth aspect, a fluid processing system is provided. The system includes a disposable fluid processing circuit comprising a fluid processing device, a reservoir, access devices for establishing fluid communication with one or more containers of a processing fluid, a reservoir, an access device for establishing fluid communication with a fluid source and tubing for establishing flow communication between processing device, reservoir, said one or more containers, and said fluid source; and a reusable hardware unit for receiving said fluid processing circuit in a predetermined relationship and one or more controllers, said controller(s) comprising pre-programmed instructions for carrying out a selected fluid processing protocol and for priming said circuit according to the protocol selected.

A thirteenth aspect of the present subject matter includes the system of the twelfth aspect wherein said controller includes preprogrammed instructions for priming a portion of the circuit with a first solution and a portion of the circuit with a second solution.

A fourteenth aspect of the present subject matter includes the system of the thirteenth aspect wherein said controller includes preprogrammed instructions to carry out a biological fluid processing protocol that includes administering said second solution as a replacement fluid.

A fifteenth aspect of the present subject matter includes the system of any one of the thirteenth through thirteenth aspects including a monitor for monitoring the amount of a solution used to prime said portion of said system.

A sixteenth aspect of the present subject matter includes the system of fifteenth aspect wherein said monitor comprises a weight scale for a holding a container of said first solution.

A seventeenth aspect of the present subject matter includes the system of fifteenth aspect wherein the said monitor comprises a weight scale for a holding said reservoir.

In addition to the aspects set forth above in the Summary, the Description above and the claims that follow, there are other aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

The invention claimed is:

1. A method of priming a blood processing circuit prior to a blood processing protocol comprising:
   a) mounting a biological fluid processing circuit that includes a biological fluid processor, a reservoir, one or more containers of processing solutions, a biological fluid access device and a flow path establishing flow communication between said one or more solutions, a source of biological fluid, onto a hardware component of a biological fluid processing system in a predetermined relationship;
   b) selecting a biological fluid processing protocol;
   c) introducing a first solution from a first container of a processing solution and flowing said first solution through a portion of said processing circuit;
   d) monitoring for the presence of liquid at a detection point of said circuit;
   e) detecting the presence of liquid in said circuit at said detection point;
   f) upon said detecting, introducing a further amount of said first solution into said fluid circuit, wherein said amount is sufficient to deliver said first solution to a selected point of said flow path;
   g) introducing a fluid from a source other than said first container into said flow path and through at least a portion of said processing circuit that is different from the portion through which said first solution is flowed.

2. The method of claim 1 wherein said fluid comprises a second solution from a second container.

3. The method of claim 2 wherein said step of introducing said second solution is determined by the blood processing protocol selected.

4. The method of claim 3 wherein said selected blood processing protocol comprises returning one or more blood components to a blood source and delivering a replacement fluid to said source.

5. The method of claim 2 wherein said first solution comprises anticoagulant and said second solution comprises a replacement fluid.

6. The method of claim 5 wherein said replacement fluid comprises saline.

7. The method of claim 1 wherein said volume of said first solution is between 10 ml and 30 ml.

8. The method of claim 7 wherein said first solution includes citrate.

9. The method of claim 1 comprising monitoring the volume of said introduced first solution.

10. The method of claim 9 comprising monitoring said volume by observing changes in the weight of said first container.

11. The method of claim 9 comprising monitoring said volume by determining the number of pump strokes in a pump associated with said introduced first solution.

12. The system of claim 1 wherein said fluid is blood.

13. The system of claim 12 wherein said controller is configured to deliver said blood to said different portion of said processing circuit.

14. The method of claim 1 further comprising selecting a biological fluid processing protocol from a first protocol wherein a replacement fluid is administered to a subject and a second protocol wherein no replacement fluid is administered to the subject.

15. The method of claim 1 comprising selecting a biological fluid processing protocol from a first protocol wherein saline is used to prime at least a portion of the fluid circuit and a second protocol wherein saline is not used to prime the fluid circuit.

16. A blood processing system comprising:
a) a disposable fluid processing circuit comprising a fluid processing device, a reservoir, access devices for establishing fluid communication with one or more containers of a processing fluid, a reservoir, an access device for establishing fluid communication with a fluid source and tubing defining a flow path for establishing flow communication between processing device, reservoir, said one or more containers, and said fluid source; and
b) a reusable hardware unit for receiving said fluid processing circuit in a predetermined relationship comprising a detector for detecting the presence of fluid within said liquid circuit and, a controller being in communication with said detector, said controller further comprising pre-programmed instructions for carrying out a selected blood processing protocol and configured to effect priming of said circuit according to the protocol selected, wherein said controller is further configured to effect introduction of an amount of a first solution from a first container of a processing solution and flow said first solution through a portion of said processing circuit and to introduce a further amount of said solution from said first container when the presence of liquid is detected by said detector, wherein said further amount is selected to deliver said first solution to a selected point of said flow path.

17. The system of claim 16 wherein said controller includes preprogrammed instructions for priming a portion of said circuit with a first solution and a portion of said circuit with a second solution.

18. The system of claim 17 wherein said controller includes preprogrammed instructions to carry out a blood processing protocol that includes administering said second solution as a replacement fluid.

19. The system of claim 17 further comprising a monitor for monitoring the amount of a solution used to prime said portion of said circuit.

20. The system of claim 19 wherein said monitor comprises a weight scale for a holding a container of said first solution.

21. The system of claim 19 wherein said monitor comprises a weight scale for a holding said reservoir.

22. The system of claim 16 wherein said controller is configured to introduce a fluid from a source other than said first container into said flow path and through at least a portion of said processing circuit that is different from the portion through which said first solution is flowed.

23. The system of claim 16 wherein said controller comprises pre-programmed instructions for carrying out two blood processing protocols and for priming said circuit according to the protocol selected.

24. The system of claim 23 wherein said two protocols include a first protocol wherein a replacement fluid is administered to a subject and a second protocol wherein no replacement fluid is administered to the subject.

* * * * *